United States Patent [19]

Sohda et al.

[11] Patent Number: 5,302,608
[45] Date of Patent: Apr. 12, 1994

[54] AGE FORMATION INHIBITORS

[75] Inventors: Takashi Sohda, Takatsuki; Hitoshi Ikeda, Higashiosaka; Yu Momose, Neyagawa, all of Japan

[73] Assignee: Takeda Chemical Industries, Ltd., Osaka, Japan

[21] Appl. No.: 71,036

[22] Filed: Jun. 2, 1993

Related U.S. Application Data

[63] Continuation of Ser. No. 707,300, May 29, 1991, abandoned, which is a continuation of Ser. No. 437,897, Nov. 17, 1989, abandoned.

[30] Foreign Application Priority Data

Nov. 18, 1988 [JP] Japan .................. 63-293105
Aug. 16, 1989 [JP] Japan .................. 1-211984

[51] Int. Cl.$^5$ .................. C07D 277/48; A61K 31/425
[52] U.S. Cl. .................. 514/371; 514/342; 546/280; 548/196
[58] Field of Search .............. 548/196; 514/371, 342; 546/280

[56] References Cited

FOREIGN PATENT DOCUMENTS 0193249 9/1986 European Pat. Off. .
190880 3/1988 Japan .

OTHER PUBLICATIONS

G. Ramachandraiah et al., "Synthesis of 2-aroylimino-5-arylthiazo[3,2-b]-1,2,4-thiadiazolines", Chemical Abstracts, vol. 108, No. 9, Feb. 29, 1988, p. 673, abstract no. 75304j, Columbus, Ohio.
M. Nagano et al., "Organic Sulfur Compounds, XI. Synthesis of 2-alkylthiothiazolo[3.2-alpha]-2--triazine-4-ones", Chemical Abstracts, vol. 78, No. 18, May 7, 1973, pp. 474-475, abs. no. 12448m.
Sumiuki Akihama et al., "Antiviral activity of Thiazole-thiourea Derivatives", Chemical Abstracts, vol. 67, No. 23, Dec. 4, 1967, p. 9986, abstract no. 106086f, Columbus, Ohio.
G. Ramachandraiah et al., "Synthesis of 2-Aroylimino-5-Arylthiazolo[3,2-b]-1,2,4-thiadiazolines", Sulfur Lett., vol. 6, No. 1, pp. 1-6 (1987). (Abstract only).
K. C. Satpathy et al., "Metal Complexes of N-benzoyl-N'-(4-phenyl-thiazol-2-yl)thiocarbamide as Potential Fungicides", Indian J. Chem. Sect., a 1981, 20A(6), pp. 612-614. (Abstract only).
H. H. Al-Nima et al., "Reaction of 2-aminobenzothiazole and 3-amino-5-methylisoxazole with isothiocyanates", J. Iraqi Chem. Soc., vol. 11, No. 1, pp. 13-24 (1986). (Abstract only).
Giri, Bokin Bobai 11, 575 (1983) Abstract Only.
Elnagdi, J. Heterocyclic Chemistry, 16 61 (1979).
Nagano, Chem. Pharm. Bull 20, 2626 (1972).
Badachikar, Ind. J. Chem. 24B 228 (1985).

*Primary Examiner*—Robert Gerstl
*Attorney, Agent, or Firm*—Wegner, Cantor, Mueller & Player

[57] ABSTRACT

Thiourea compounds represented by the general formula:

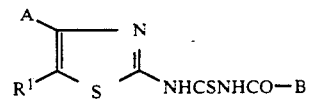

wherein A is an aromatic ring group which may be substituted; $R^1$ is a hydrogen atom or a lower alkyl or aryl group which may be substituted, or may combine with A to form a cyclic ring; and —COB is an acyl group of a carboxylic acid or an esterified carboxyl group or salts thereof are provided as agents for inhibiting the formation of AGE (Advanced Glycosidation End Product), which are employable for treating diseases caused by AGE-formation, such as diabetic complications, senile cataract, atherosclerosis etc.

14 Claims, No Drawings

AGE FORMATION INHIBITORS

This application is a continuation of U.S. application Ser. No. 07/707,300 filed May 29, 1991, which is a continuation of U.S. application Ser. No. 07/437,897 filed Nov. 17, 1989, both now abandoned.

This invention relates to thiourea derivatives or drugs containing the same and in particular to AGE-formation inhibitory agents.

In recent years, increased attention has been attracted to products of proteins glycosylated by nonenzymatic glycosylation, which are considered to be responsible for a variety of pathogenesis related to diabetes and arteriosclerosis. Nonenzymatic glycosylation involves the nonenzymatic attachment through a Schiff base of blood glucose to protein amino groups by way of a simple reaction, followed by Amadori rearrangement to form relatively stable ketoamine derivatives (1-amino-1-deoxyfructose), which cause changes in the structure and function of proteins. The resultant Amadori rearrangement products, in the course of several months to several years, further undergo dehydration and rearrangement to turn irreversibly into glucose derivatives named "AGE (advanced glycosylation end products)". AGE are yellowish brown and fluorescent, and easily bind with adjacent proteins to form crosslinks. The proteins, which have formed crosslinks through AGE, are thought to cause disturbances in various tissues. In diabetes, the nonenzymatic glycosylation of proteins increases in proportion to blood glucose levels, and this is regarded as one of the causes for diabetic complications [A. Cerami et al., "Metabolism" 28 (Suppl. 1), 431 (1979): V. Monnier et al., "New England Journal of Medicine" 314, 403 (1986)]. The process is also considered to be responsible for aging. For example, senile cataract involves the AGE formation of crystallins which are protein existing in the crystalline lens of the eye. Furthermore, crisis of atherosclerosis is associated with the AGE formation. It has been confirmed that AGE are involved in the thickening of capillary basement membranes associated with aging and the thickening of glomerular basement membrane which is responsible for renal insufficiency or failure [M. Brownlee et al., "Science", 232, 1629 (1986)].

M. Brownlee et al. reported that aminoguanidine can prevent the transformation of an Amadori rearrangement product into AGE [M. Brownlee et al., "Science", 232, 1629 (1986)], and the compound is noted as a candidate drug which is preventive against diseases associated with aging.

However, aminoguanidine as mentioned above cannot always be said to demonstrate adequate preventive or inhibitory activity, and no satisfactory, potent AGE-formation inhibitory agent has been so far found. This invention has for its object to provide compounds, which possess AGE-formation inhibitory activity and are useful as a preventive and therapeutic agent for diabetic complications and atherosclerosis, and drugs containing the same.

The present inventors, after extensive research on compounds being useful for the prevention of the above-mentioned diseases through inhibition of AGE formation, found that the thiourea derivatives of this invention to be described below possess potent inhibitory activity against AGE formation, and have completed this invention The present invention relates to a thiourea compound represented by the general formula:

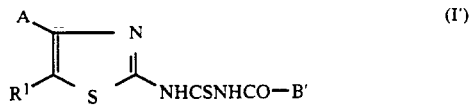

wherein A is an aromatic ring group which may be substituted; $R^1$ is a hydrogen atom or a lower alkyl or aryl group which may be substituted, or may combine with A to form a cyclic ring group; and —COB' is an acyl group of a carboxylic acid or an esterified carboxyl group; provided that, when A is an unsubstituted or substituted phenyl or A combines with $R^1$ to form a cyclic ring, B' is not an unsubstituted or substituted phenyl (hereinafter referred to in some instances as "Compound (I')" and their pharmaceutically acceptable salts, method for use thereof, and a method of using an AGE-formation inhibitory composition containing a thiourea compound of the formula:

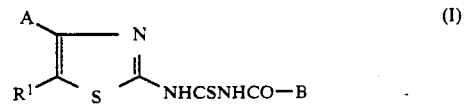

[wherein A is an aromatic ring group which may be substituted; $R^1$ is a hydrogen atom, or a lower alkyl or aryl group which may be substituted, or combines with A to form a ring; and —COB is a carboxylic acid acyl or esterified carboxyl group] (hereinafter referred to in some instances as "Compound (I)") or its salts, which can be incorporated in pharmaceutical or veterinary preparations using acceptable carriers.

As apparent from the formulas (I') and (I), Compound (I') is encompassed in Compound (I). Hereinafter, reference to Compound (I) includes reference to Compound (I'), and reference to B also includes reference to B'.

Referring to the above-mentioned formulas (I) and (I'), the aromatic ring group as represented by A which may be substituted includes aromatic carbocyclic ring groups and aromatic heterocyclic ring groups which may be respectively substituted. As the aromatic carbocyclic ring groups, there are preferred $C_{6-14}$ aryl, such as phenyl, naphthyl and anthryl. Such naphthyl, anthryl, etc. may have rings partly saturated. In addition, the aromatic ring group includes such $C_{6-14}$ aryls which are condensed with the below-mentioned aromatic heterocyclic ring directly or after being partly or wholly saturated.

The aromatic heterocyclic ring group is preferably a 5- to 6-membered aromatic heterocyclic ring group containing 1 to 4 of nitrogen, oxygen, sulfur, etc. as a ring-forming heteroatom, and includes not only monocyclics but also polycyclics or heterocyclic rings being condensed with carbocyclic groups as well. The terms "heterocyclic ring" and "carbocyclic ring" comprehend not only the aromatic heterocyclic rings and aromatic carbocyclic rings as described above but also rings derived by saturating these heterocyclic and carbocyclic rings wholly or partly. Specific examples of such aromatic heterocyclic ring groups include 2-, 3- or 4-pyridyl, 2-or 3-thienyl, 2- or 3-furyl 2- or 3-pyrrolyl, 2-, 4- or 5-imidazolyl, 3-, 4- or 5-pyrazolyl, 3-, 4-or 5-isothiazolyl, 3-, 4- or 5-isoxazolyl, 2-, 4- or 5-thiazolyl, 2-, 4- or 5-oxazolyl, 2- or 3-pyrazinyl, 2-, 4-, 5- or 6-pyrimidyl, 3-4- or pyridazinyl, 1-, 3- or 4-isoquinolyl, 2-, 3- or 4-quinolyl, 2- or 4-quinazolyl, 2-benzimidazolyl, 2-benzoxazolyl, 2-benzothiazolyl,2-or 3-benzofuryl, 2- or 3-benzothienyl, 2- or 3-indolyl and the like. Among these, preferred as the symbol A are particularly aromatic carbocyclic ring groups which may be substituted, and condensed aromatic ring groups are preferable. The condensed aromatic ring groups mean the polycyclic ring groups comprising two or more rings of the above-mentioned aromatic rings, which are condensed with each other. Such condensed aromatic ring groups include condensed ring groups of aromatic heterocyclic rings, those of aromatic carbocyclic rings and those of aromatic heterocyclic (or carbocyclic) rings which are partially saturated. More preferred as A are condensed aromatic ring groups which may be substituted. Above all preferred are phenyls or naphthyls which may be substituted. More particularly suitable as the symbol A are partly saturated naphthyls (e.g. 5,6,7,8-tetrahydro-2-naphthyl).

As the lower alkyl which may be substituted, as represented by $R^1$, straight-chain, branched and cyclic $C_1$ to $C_{10}$ alkyls are preferable, and their examples include methyl, ethyl, propyl, isopropyl, butyl, isobutyl, sec-butyl, pentyl, isopentyl, hexyl, heptyl, octyl, nonyl, cyclopropyl, cyclobutyl, cyclopentyl, cyclohexyl and the like.

As the aryl which may be substituted, as represented by $R^1$, there may be mentioned, for example, $C_{6-10}$ aryls, such as phenyl, naphthyl and anthryl.

$R^1$ may combine with A to form a ring, and the ring containing a thiazole ring, which $R^1$ can combine with A to form, includes for example 4,5-dihydronaphtho[1,2-d]thiazole, 4,5-dihydrophenanthro[4,3-d]thiazole, 10,11-dihydrophenanthro[1,2-d]thiazole, indeno[5,4-d]thiazole, 5,6-dihydro-4H-benzo[6,7]cyclohepta[1,2-d]thiazole, 4,5-dihydrothiazolo[5,4-h]quinoline and the like.

As the symbol B in cases where —COB represents an esterified carboxyl group, particularly, groups designated by $OR^2$ (wherein $R^2$ is a hydrocarbon residue which may be substituted) are preferred.

The hydrocarbon residue which may be substituted, as represented by $R^2$, includes for example alkyl, aralkyl, aryl, alkenyl, arylalkenyl and alkynyl groups which may be individually substituted. As the alkyl which may be substituted, as represented by $R^2$, more specifically, there may be mentioned for example $C_1$ to $C_{10}$ straight-chain, branched or cyclic alkyl groups, such as methyl, ethyl, propyl, isopropyl, cyclopropyl, butyl, isobutyl, sec-butyl, tert-butyl, cyclobutyl, pentyl, isopentyl, neopentyl, cyclopentyl, hexyl, cyclohexyl, heptyl, cycloheptyl, octyl, nonyl and decyl.

As the aralkyl which may be substituted, as represented by $R^2$, phenyl-$C_{1-4}$-alkyls, such as benzyl, phenethyl, 3-phenylpropyl and 4-phenylbutyl, are preferred.

The aryl which may be substituted, as represented by $R^2$, includes for example $C_{6-14}$ aryls, such as phenyl, naphthyl and anthryl. The alkenyl represented by $R^2$ includes for example $C_{1-4}$ alkenyls, such as vinyl, allyl and isopropenyl, and the arylalkenyl which may be substituted, as represented by $R^2$, includes for example $C_{1-6}$ alkenyls having an aromatic ring group attached thereto, such as cinnamoyl, 3-(2-pyridyl)acryloyl, 3-(3-pyridyl)acryloyl, 3-(2-furyl)acryloyl and 4-phenyl-2-butenoyl. The alkynyl represented by $R^2$ for example $C_{1-4}$ alkynyls, such as ethynyl and propynyl. As $R^2$, among the above-mentioned groups, alkyls, aralkyls and aryls which may be individually substituted are particularly preferable.

As the symbol B in cases where —COB represents an acyl group of a carboxylic acid, saturated or unsaturated aliphatic groups which may be substituted or aromatic ring groups which may be substituted are particularly preferred. Such saturated or unsaturated aliphatic groups which may be substituted include for example alkyl, alkenyl, alkynyl, aralkyl or arylalkenyl groups which may be individually substituted. As these alkyl, alkenyl, alkynyl, aralkyl and arylalkenyl groups, there may be directly used the alkyl, alkenyl, alkynyl, aralkyl and arylalkenyl groups as mentioned above for $R^2$.

As the aromatic ring group which may be substituted, as represented by B, there are directly used the aromatic ring groups as mentioned above for A.

As the substituent in the above-mentioned aromatic ring groups which may be substituted, as represented by the symbols A and B, there may be mentioned for example alkyls, hydroxyls, thiols, alkanoyls, aminos, acylaminos or aromatic ring groups, halogens, or cyano, alkoxycarbonyls or aryloxycarbonyl and nitro groups which may be individually substituted, and the said aromatic ring groups may be substituted by 1 to 4 of these substituents. The alkyl as the said substituent in the aromatic ring group represented by the symbol A or B includes for example $C_{1-10}$ straight-chain, branched or cyclic alkyl groups, such as methyl, ethyl, propyl, isopropyl, cyclopropyl, butyl, isobutyl, sec-butyl, tert-butyl, cyclobutyl, pentyl, isopentyl, neopentyl, cyclopentyl, hexyl, cyclohexyl, heptyl, cycloheptyl, octyl, nonyl and decyl. These alkyl groups may be substituted particularly by 1 to 3 of halogens and the like.

The hydroxyl group which may be substituted, as the substituent in the aromatic ring groups represented by the symbol A or B, includes for example hydroxyl and suitably substituted hydroxyls, especially those having a substituent used normally as a protective group for hydroxyl, such as alkoxy, aralkyloxy and acyloxy. Preferable examples of the said alkoxy include alkoxys (e.g., methoxy, ethoxy, propoxy, isopropoxy, cyclopropoxy, butoxy, isobutoxy, sec-butoxy, tert-butoxy, cyclobutoxy, pentoxy, isopentoxy, neopentoxy, cyclopentoxy, hexyloxy, cyclohexyloxy, heptyloxy, cycloheptyloxy, octyloxy, nonyloxy, decyloxy, etc.) having $C_{1-10}$ straight-chain, branched and cyclic alkyl groups as mentioned above. Preferred examples of the said aralkyloxy include for example phenyl-$C_{1-4}$ alkoxys (e.g., benzyloxy, phenethyloxy, 3-phenylpropoxy, etc.). As the said acylxoy, $C_{2-8}$ alkanoyloxys (e.g., acetyloxy, propionyloxy, n-butyryloxy, iso-butyryloxy, valeryloxy, cyclopentanecarbonyloxy, caproyloxy, cyclohexanecarbonyloxy, heptanoyloxy, cycloheptanecarbonyloxy, etc.) are preferable. Examples of the thiol group which may be substituted, as the substituent in the aromatic ring group represented by the symbol A or B, include thiol group and suitably substituted thiol groups, especially those having a group used normally as a protective group for thiol group, such as alkylthio, aralkylthio and acylthio. As the said alkylthio, alkylthios (e.g., methylthio, ethylthio, propylthio, isopropylthio, cyclopropylthio, butylthio, isobutylthio, sec-butylthio, tert-butylthio, cyclobutylthio, pentylthio, isopentylthio, neopentylthio, cyclopentylthio, hexylthio, cyclohexylthio, heptylthio, cycloheptylthio, octylthio, nonylthio, decylthio, etc.) having the above-mentioned $C_{1-10}$ straight-chain, branched and cyclic alkyl groups are preferable. As the said aralkylthio, there may be mentioned for example phenyl-$C_{1-4}$ alkylthios (e.g., benzylthio, phenethylthio, 3-phenylpropylthio, etc.). Particularly preferred examples of the said acylthio include $C_{2-8}$ alkanoylthios (e.g., acetylthio, propionylthio, n-butyrylthio, iso-butyrylthio, valerylthio, cyclopentanecarbonylthio, caproylthio, cyclohexanecarbonylthio, cycloheptanecarbonylthio, etc.).

Examples of the acyl as the substituent in the aromatic ring groups represented by the symbol A or B include formyl or carboxylic acid acyls (e.g., acetyl, propionyl, butyryl, isobutyryl, valeryl, isovaleryl, pivaloyl, cyclopentanecarbonyl, caproyl, cyclohexanecarbonyl, heptanoyl, cycloheptanecarbonyl, octanoyl, nonanoyl, decanoyl, etc) consisting of the above-mentioned $C_{1-10}$ alkyl bonded with a carbonyl group or $C_{2-11}$ As the substituent which these acyl groups may have, there are useful halogens, $C_{1-6}$ alkoxys and phenyls which may be substituted with halogens, $C_{1-6}$ alkyls and/or $C_{1-6}$ alkoxys.

Examples of substituted amino groups for the amino group which may be substituted, as the substituent in the aromatic ring groups represented by the symbol A or B include amino groups being substituted by 1 to 1 $C_{1-6}$ alkyls, such as methylamino, ethylamino, propylamino, isopropylamino, butylamino, pentylamino, hexylamino, dimethylamino, diethylamino, diisopropylamino and dibutylamino. The said alkyl groups may be further substituted by alkoxys, alkylthios, halogens, etc. As the substituent which the amino groups may have, there may be mentioned $C_{1-6}$ alkoxys, $C_{1-6}$ alkylthios, halogens and the like, in addition to such alkyl groups which may be substituted.

Examples of acylaminos as the substituent in the aromatic ring groups represented by the symbol A or B, include $C_{8-11}$ alkanoylamino (e.g., acetylamino, propionylamino, butyrylamino, isobutyrylamino, valerylamino, isovalerylamino, pivaloylamino, cyclopentanecarbonylamino, caproylamino, cyclohexanecarbonylamino, heptanoylamino, cycloheptanecarbonylamino, octanoylamino, nonanoylamino, decanoylamino, etc.) consisting of the above-mentioned acyls bonded with amino groups. As the substituent which these acylmino groups may have, there are mentioned halogens, $C_{1-6}$ alkoxys, $C_{1-6}$ alkylthios, hydroxyl and the like.

Examples of aromatic ring groups as the substituent in the aromatic ring groups represented by the symbols A or B include those exemplified in the above for the symbols A and B. As substituents in these aromatic rings, there may be mentioned, for example, halogens and nitro, amino, $C_{1-6}$ alkanoylamino, $C_{1-6}$ alkoxy, $C_{1-6}$ alkylthio and hydroxyl group.

Examples of the halogens include fluorine, chlorine, bromine and iodine, with fluorine and chlorine being particularly preferable.

Alkoxycarbonyl or aryloxycarbonyl groups as the substituent in the aromatic ring groups represented by the symbols A or B, include for example groups (e.g., methoxycarbonyl, ethoxycarbonyl, isopropoxycarbonyl, hexyloxycarbonyl, cyclohexyloxycarbonyl, etc.) being formed by the combination of the above-mentioned $C_{1-10}$ alkyls with carboxyl groups, and groups (e.g., phenoxycarbonyl, 2-naphthyloxycarbonyl, 4-chlorophenoxycarbonyl, etc.) being formed by the combination of $C_{6-14}$ aryls with carboxyl groups, and the alkoxycarbonyls and aryloxycarbonyls may be substituted by halogens.

As preferred examples of the aromatic ring group which may be substituted, as represented by A and B, mention is made of aromatic rings which are unsubstituted or substituted by one to four substituent(s) selected from a group $S^1$ consisting of (1) $C_{1-10}$ alkyls which may be substituted by halogens; (2) hydroxyls which may be substituted by $C_{1-10}$ alkyls, phenyl-$C_{1-4}$ alkyls, and/or $C_{2-8}$ alkanoyls; (3) thiols which may be substituted by $C_{1-10}$ alkyls, phenyl-$C_{1-4}$ alkyls and/or $C_{2-8}$ alkanoyls; (4) formyl; (5) $C_{2-11}$ alkanoyls which may be substituted by halogens, $C_{1-6}$ alkoxys and/or phenyls which may be substituted by halogens, $C_{1-6}$ alkyls and/or $C_{1-6}$ alkoxys; (6) amines which may be substituted by $C_{1-6}$ alkyls (which may be substituted by $C_{1-6}$ alkoxys, $C_{1-6}$ alkylthios and/or halogens), $C_{1-6}$ alkoxys, $C_{1-6}$ alkylthios and/or halogens); (7) $C_{2-11}$ alkanoylaminos which may be substituted by halogens, $C_{1-6}$ alkoxys, $C_{1-6}$ alkylthios and/or hydroxyl; (8) aromatic rings which may be substituted by halogens, nitro, amino, $C_{1-6}$ alkanoylamino, $C_{1-6}$ alkoxyls, $C_{1-6}$ alkylthios, and/or hydroxyl; (9) halogens; (10) cyano; (11) $C_{2-11}$ alkoxycarbonyl which may be substituted by halogens, (12) $C_{6-14}$ aryloxycarbonyl which may be substituted by halogens; and (13) nitro.

Substituents in the aryl groups which may be substituted, as represented by $R^1$, include for example the above-mentioned substituents (namely, the alkyl, hyroxyl, thiol, acyl and acylamino groups, halogens and cyano groups, which may individually be substituted) in the aromatic ring groups represented by the symbols A and B. Preferred Examples of the substituents in the aryl groups, as represented by $R^1$ are the same as mentioned above for A and B. The said aryl groups may have 1 to 3 of these substituents, and such substituted aryl groups include for example 4-chlorophenyl, 4-fluorophenyl, methylphenyl, 3,4-dimethoxyphenyl, 3,4-methylenedioxyphenyl, 2,4-dichlorophenyl, 4-acetylaminophenyl, 4-benzyloxyphenyl, 2-cyanophenyl and 4-benzylthiophenyl.

Substituents in the lower alkyl group which may be substituted, as represented by $R^1$, include for example phenyl groups (which may be substituted by the substituents exemplified in the above for the substituents in the aryl groups which may be substituted, as represented by $R^1$, and particularly unsubstituted phenyl is preferable), halogens and $C_{1-6}$ alkoxy, $C_{1-6}$ alkylthio and $C_{2-8}$ alkanoylamino groups. The lower alkyl groups represented by $R^1$ may have 1 to 3 of these substituents.

Salts of the Compound (I) include for example acid salts formed with hydrochloric acid, sulfuric acid, acetic acid, citric acid, maleic acid, fumaric acid, etc., which are pharmaceutically acceptable in relation to the thiazole ring or basic groups in the symbols A and B, or salts formed between the -NHCSNH- group and alkali metals such as sodium and potassium.

The above-mentioned Compounds (I) or their salts can be produced for example by the following reaction.

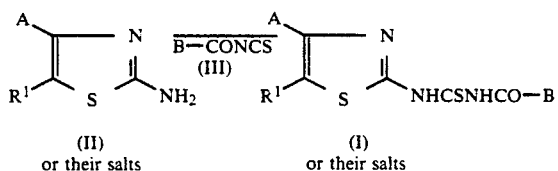

(II) or their salts     (I) or their salts

[wherein A, B and $R^1$ are as defined in the above].

Thus, an aminothiazole derivative (II) or its salts and an isothiocyanate derivative (III) can be heated in the presence or absence of solvent to produce Compound (I) or its salt. The salts of (II) as used herein include for example acid salts (e.g., hydrochlorides, sulfates, acetates, etc.) formed in relation to the amino group or basic groups in A. Examples of such solvent include ethers, as dioxane, tetrahydrofuran and dimethoxyethane; aromatic carbons, such as benzene, toluene and xylene; ethyl acetate, acetonitrile, pyridine, N,N-dimethylformamide, dimethylsulfoxide, chloroform, dichloromethane, 1,2-dichloroethane, 1,1,2,2-tetrachloroethane, acetone or solvent mixtures thereof. The reaction temperature ranges from about 0° C. to about 150° C., preferably from about 10° C. to 100° C., while the reaction time is normally in the region of 0.1 to 50 hours, preferably 0.5 to 20 hours.

The thiourea compounds (I) as obtained in this manner can be isolated and purified by the known separation and purification means, such as concentration, vacuum concentration, solvent extraction, crystallization, recrystallization, solvent transfer and chromatography.

The aminothiazole derivatives (II) as used in the above-described production method can be produced for example by means of the methods, or methods similar thereto, as described in Chemical Abstracts, 53 14089e (1959); Chemical Abstracts, 105 221003s (1986); European Journal of Medicinal Chemistry, 16 355 (1981); Shin-Zikken Kagaku Kohza (New Discourses on Experimental Chemistry), 14 "Synthesis and Reactions of Organic Compounds [IV]" (1976) and the like.

Since the thiourea compounds (I) or their salts possess excellent AGE-formation inhibitory activity, they can be utilized as drugs for human beings and livestock or domestic animals, and are safely usable as an AGE-formation inhibitory agent being capable of treating and preventing a great variety of diseases caused by the transformation of proteins into AGE.

The thiourea compounds (I) or their salts, alone or in combination with other active components, can be admixed with adjuvants, such as neutralizing agents, stabilizers and dispersing agents, if necessary, and processed into pharmaceutical preparations for clinical use, such as capsules, tablets, powders, solutions, suspensions or elixirs, in accordance with the conventional procedures. These can be administered parenterally (e.g., rectal administration) or orally.

The thiourea compounds (I) or their salts, after being suitably admixed with binding agents, such as syrup, gum arabic, gelatin, sorbitol, gum tragacanth and polyvinylpyrrolidone; fillers, such as lactose, sugars, corn starch, calcium phosphate, sorbitol and glycine; lubricants, such as magnesium stearate, talc, polyethylene glycol and silica disintegrating agents, such as potato starch; or wetting agents, such as sodium lauryl sulfate, can be processed into oral dosage forms, such as tablets, capsules, granules and powders. Tablets, granules, etc. can also be provided with film coating by the per se known procedures. Such pharmaceutical preparations for oral administration may be used in the form of liquid dosage forms, such as aqueous or oily suspensions, solutions, emulsions, syrups and elixirs.

Pharmaceutical preparations for rectal administration containing the thiourea compounds (I) or their salts are produced by mixing excipients for suppositories, additives and the thiourea compounds (I) or their salts and processing the mixture into, for example, oily solid suppositories, semi-solid ointment-like suppositories and capsule suppositories having liquid compositions filled into soft capsules. The proportions, in which the thiourea compounds (I) or their salts are used against the total pharmaceutical preparation, are normally selected from the range from about 0.5 to 50 weight %, but are not understood to be limited to such range. In this invention, other nonionic surfactants, such as polyoxyethylene fatty acid esters and polyoxyethylene higher alcohol ethers, may be used simultaneously in such pharmaceutical preparations or anionic surfactants can also be incorporated into them, in order to enhance the absorption of the thiourea compounds (I) or their salts or to control their absorption rates. So as to increase the solubilities or stabilities of the thiourea compounds (I) or their salts, furthermore, numerous salts or stabilizing agents can also be incorporated into or admixed with them. In addition, dispersing agents, preservatives and the like can be added, if pharmaceutically required.

Also, these pharmaceutical preparations may be incorporated with other components, such as the known antioxidants, preservatives, lubricants, viscosity-increasing agents and flavors, in accordance with the conventional procedures. Furthermore, these pharmaceutical preparations can be admixed with other active ingredients to process into the intended pharmaceutics which exhibit AGE-formation inhibitory activity.

The thiourea compounds (I) or their salts can be used as an AGE-formation inhibitory agents for the treatment and prevention of such diseases in human beings and mammals as diabetic complications, senile cataract, atherosclerosis and the thickening of glomerular basement membrane. The thiourea compounds (I) or their salts are administered in varied daily doses depending upon the conditions and body weight of patients, route of administration and the like, and can be given to adult patients parenterally in the doses as an active ingredient (the thiourea compounds (I) or their salts) of about 0.05 to 80 mg per kg of body weight, preferably about 0.1 to 10 mg, suitably through rectal administration as divided into twice to 4 times daily, while they can suitably be applied orally to adult patients in the doses as an active ingredient (the thiourea compounds (I) or their salts) of about 0.5 to 100 mg, preferably 1 mg to 30 mg, per kg of body weight, as divided into once to 3 times daily.

It is to be added that the thiourea compounds (I) or their salts, after being administered, exhibit excellent distribution throughout the body, being substantially free from side-effects, and constitute the ideal AGE-formation inhibitory agent being capable of producing improved therapeutic and preventive effects against the diseases brought about by the transformation of proteins into AGE.

The thiourea compounds (I) or their salts demonstrate excellent inhibitory activity against the production of the transformed substances (AGE) of glycosylated proteins.

EXPERIMENT EXAMPLE

The production of advanced glycosylated end products (AGE) and its measurement were carried out in accordance with the report by Brownlee et at. [Science, 232 1629 (1986)]. Thus, bovine serum albumin (fraction V, manufactured by Wako Pure Chemical Ind. of Japan, 20%), D-glucose (100 mM) and sodium azide (3 mM) were dissolved in 0.5M phosphate buffer (pH 7.4) to prepared a reaction solution (control). A test specimen was dissolved in dimethyl sulfoxide, and the solution was added to the reaction solution to the concentrations 1 mM, 0.5 mM and 0.2 mM, respectively. These solutions were incubated at 37° C. for 7 days, whereupon the solutions, before and after incubation, were diluted with phosphate buffer, followed by measurement of fluoresceces (by use of RF-510 spectrofluorimeter, manufactured by Shimadzu Seisakusho of Japan) at 370 nm excitation wavelength and 440 nm emission wavelength. The variation in fluorescence (F) was utilized to calculate the formation ratio (%) following the formula described below. In the above tests, the blind test was carried out using the reaction solution free from D-glucose. The AGE were calculated by the following equation:

$$\text{Formation ratio} = [F(T) - F(B)]/[F(C) - F(B)] \times 100$$

where F(T), F(B) and F(C) are variations in fluorescence for test specimen, blind test specimen and control, respectively.

Shown in Table 1 are the measurement results obtained by the method.

TABLE 1

| Compound Example No. | AGE Formation Ratio (% against the control value) |
|---|---|
| 1 | 43[2] |
| 4 | 47[1] |
| 8 | 58[1] |
| 10 | 30[1] |
| 11 | 66[1] |
| 13 | 15[1] |
| 15 | 46[2] |
| 20 | 0[2] |
| 21 | 19[2] |
| 22 | 31[1] |
| 23 | 51[1] |
| 26 | 34[2] |
| 27 | 0[1] |
| 31 | 53[2] |
| 34 | 0[2] |
| 37 | 49[1] |
| 42 | 35[2] |
| 47 | 16[1] |
| 52 | 32[2] |
| 53 | 67[3] |
| 56 | 26[2] |
| 60 | 17[2] |
| 63 | 54[1] |
| 68 | 65[3] |
| 72 | 58[1] |

Note:
[1] Concentration of test specimen: 1 mM.
[2] Concentration of test specimen: 0.5 mM.
[3] Concentration of test specimen: 0.2 mM.

As is evident from the above results, addition of the Compounds (I) or their salts to the reaction solution led to reduced formation of AGE, as compared with the control (AGE formation ratio = 100%), and consequently, the Compounds (I) or their salts are found to possess excellent AGE-formation inhibitory activity.

The thiourea compounds (I) or their salts according to this invention, as is obvious from the above experiment example, possess excellent AGE-formation suppressive or inhibitory activity, and consequently, this invention can provide a novel AGE-formation inhibitory agent being useful for the prevention and treatment of the diseases caused by the transformation of proteins into AGE.

Described in the following are the examples to illustrates this invention in more particular, but this invention is not understood to be limited to them. In the examples, the melting points as stated all were as measured by the hot plate method and not corrected, while the symbols Me and Et as described in the following description stand for methyl and ethyl groups, respectively.

EXAMPLE 1

A mixture consisting consisting of 2-amino-4-(5,6,7,8-tetrahydro-2-naphthyl)thiazole (500 mg), benzoylisothiocyanate (363 mg) and acetone (10 ml) was stirred at 55° to 60° C. for 3 hours and then concentrated under reduced pressure. The residue was treated with ether, and the resultant crystals were recrystallized from chloroform-ethanol to produce 1-benzoyl-3-[4-(5,6,7,8-tetrahydro-2-naphthyl)-2-thiazolyl] thiourea (yield of 583 mg, 68.2%) in the form of colorless prisms. m.p., 181°–182° C.

Elemental analysis as $C_{21}H_{19}N_3OS_2$: Calculated values C, 64.09; H, 4.87; N, 10.68. Found values; C, 63.96; H, 4.84; N, 10.69.

EXAMPLES 2 THROUGH 22

By following the same procedure as described in Example 1, there were obtained the compounds as shown in Table 2.

EXAMPLE 23

4-Chlorobenzoyl chloride (911 mg) was added to a solution of ammonium thiocyanate (460 mg) in acetone (20 ml), and the solution mixture was heated over a water bath for 1 minute and stirred at room temperature for 1 hour. A solution of 2-amino-4-(5,6,7,8-tetrahydro-2-naphthyl)thiazole (1.0 g) in acetone (10 ml) was added to the solution, followed by stirring at room temperature for 16 hours. The reaction mixture was poured into water, and the crystals which separated out were recovered by filtration and washed with water and hexane, successively. Recrystallization from dichloromethane-ethanol produced 1-(4-chlorobenzoyl)-3-[4-(5,6,7,8-tetrahydro-2-naphthyl-)2-thiazolyl]thiourea (Yield of 1.08 g, 58.1%) %) in the form of colorless needles. m.p. 193° to 194° C.

Elemental analysis as $C_{21}H_{18}ClN_3OS_2$: Calculated values; C, 58.94; H, 4.24; N, 9.82. Found values: C, 58.69; H, 4.14; N, 9.73.

EXAMPLES 24 THROUGH 39

By following the same procedure as described in Example 23, there were obtained the compounds as shown in Table 3.

TABLE 2

$$\underset{R^1}{\overset{A}{\diagdown}}\underset{S}{\diagup}\underset{}{\diagdown}\underset{NHCSNHCO-B}{\overset{N}{\diagdown}}$$

| Example No. | A | B | R¹ | Yield % | Recryst'n. solvent | m.p. °C. |
|---|---|---|---|---|---|---|
| 2 | tetrahydronaphthyl | OEt | H | 89.2 | CH₂Cl₂-Hexane | 180–181 |
| 3 | tetrahydronaphthyl | phenyl | Me | 70.1 | CH₂Cl₂-EtOH | 185–186 |
| 4 | 4-Me-phenyl | phenyl | H | 82.9 | CH₂Cl₂-EtOH | 216–217 |
| 5 | 3,4-diMe-phenyl | phenyl | H | 84.5 | CH₂Cl₂-EtOH | 209–210 |
| 6 | indanyl | phenyl | H | 70.1 | CH₂Cl₂-EtOH | 189–190 |
| 7 | benzocycloheptyl | phenyl | H | 83.5 | CH₂Cl₂-EtOH | 159–160 |
| 8 | 4-CF₃-phenyl | phenyl | H | 84.5 | CH₂Cl₂-EtOH | 231–232 |
| 9 | 4-cyclohexyl-phenyl | phenyl | H | 82.7 | CH₂Cl₂-EtOH | 219–220 |
| 10 | 4-Cl-phenyl | phenyl | H | 66.4 | CHCl₃-EtOH | 222–223 |
| 11 | 3-Me-phenyl | phenyl | H | 72.2 | CHCl₃-EtOH | 219–220 |
| 12 | 3,4-diMeO-phenyl | phenyl | H | 60.6 | CHCl₃-EtOH | 225–226 |
| 13 | 3,4-(OCH₂CH₂O)-phenyl | phenyl | H | 73.6 | CHCl₃-EtOH | 224–225 |

TABLE 2-continued

Structure:
A\\C=N  
R¹/C-S-C(NHCSNHCO—B)

| Example No. | A | B | R¹ | Yield % | Recryst'n. solvent | m.p. °C. |
|---|---|---|---|---|---|---|
| 14 | furan-2-yl | phenyl | H | 69.1 | CH₂Cl₂-EtOH | 213–214 |
| 15 | naphthalen-2-yl | phenyl | H | 85.4 | CH₂Cl₂-EtOH | 213–214 |
| 16 | 2-phenyl-5-methyl-oxazol-4-yl | phenyl | H | 70.1 | CH₂Cl₂-EtOH | 228–229 |
| 17 | pyridin-2-yl | phenyl | H | 72.8 | CH₂Cl₂-EtOH | 207–208 |
| 18 | pyridin-3-yl | phenyl | H | 98.8 | CH₂Cl₂-EtOH | 204–205 |
| 19 | thien-2-yl | phenyl | H | 70.8 | CH₂Cl₂-EtOH | 195–196 |
| 20 | 5,6,7,8-tetrahydronaphthalen-2-yl | phenyl | Et | 63.3 | CH₂Cl₂-EtOH | 187–188 |
| 21 | 5,6,7,8-tetrahydronaphthalen-2-yl | phenyl | —CHMe₂ | 60.2 | CH₂Cl₂-EtOH | 186–188 |
| 22 | 5,6,7,8-tetrahydronaphthalen-2-yl | biphenyl | | 67.6 | CH₂Cl₂-EtOH | 202–203 |

TABLE 3

Structure:
A\\C=N  
R¹/C-S-C(NHCSNHCO—B)

| Example No. | A | B | R¹ | Yield % | Recryst'n. solvent | m.p. °C. |
|---|---|---|---|---|---|---|
| 24 | phenyl | phenyl | H | 58.8 | CH₂Cl₂-EtOH | 208–209 |

TABLE 3-continued
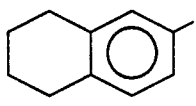
| Example No. | A | B | R¹ | Yield % | Recryst'n. solvent | m.p. °C. |
|---|---|---|---|---|---|---|
| 25 | 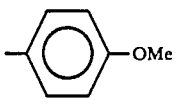 | 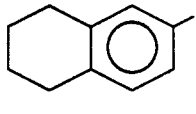 —OMe | H | 53.9 | $CH_2Cl_2$-EtOH | 198–199 |
| 26 | 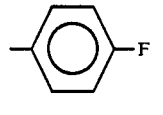 | 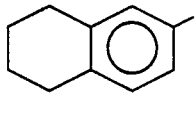 —F | H | 47.4 | $CH_2Cl_2$-EtOH | 217–218 |
| 27 | 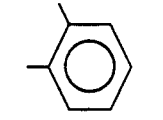 | 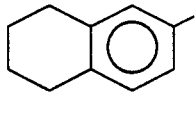 Me | H | 56.5 | $CH_2Cl_2$-EtOH | 196–197 |
| 28 | 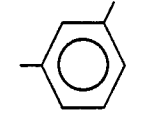 | 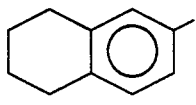 Me | H | 55.4 | $CH_2Cl_2$-EtOH | 158–159 |
| 29 | 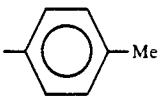 | 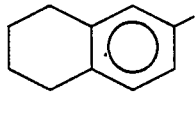 —Me | H | 57.6 | $CH_2Cl_2$-EtOH | 198–199 |
| 30 | 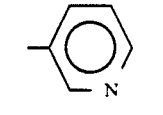 | 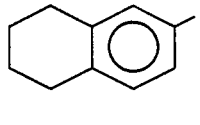 | H | 32.0 | $CH_2Cl_2$-EtOH | 226–227 |
| 31 | 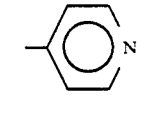 | 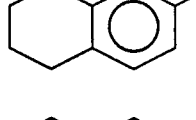 | H | 21.1 | $CH_2Cl_2$-EtOH | 218–219 |
| 32 | 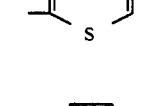 | 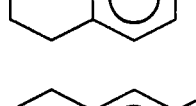 | H | 66.2 | $CH_2Cl_2$-EtOH | 218–219 |
| 33 | 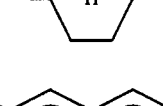 | 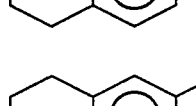 H | H | 14.6 | $CH_2Cl_2$-EtOH | 228–229 |
| 34 | 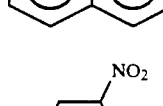 | 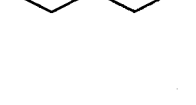 | H | 40.0 | $CH_2Cl_2$-EtOH | 215–216 |
| 35 |  | $NO_2$ (on phenyl) | H | 67.2 | $CH_2Cl_2$-EtOH | 219–220 |

TABLE 3-continued $$\underset{R^1}{\overset{A}{\diagdown}}\underset{S}{\diagup}\underset{}{\overset{}{\diagdown}}\underset{}{\overset{N}{\diagup}}\text{NHCSNHCO}-B$$

| Example No. | A | B | $R^1$ | Yield % | Recryst'n. solvent | m.p. °C. |
|---|---|---|---|---|---|---|
| 36 | tetrahydronaphthyl | phenyl-$NO_2$ | H | 61.2 | $CH_2Cl_2$-EtOH | 217–218 |
| 37 | tetrahydronaphthyl | CH=CH-phenyl | H | 56.5 | $CH_2Cl_2$-EtOH | 125–126 |
| 38 | tetrahydronaphthyl | CH=CH-$CH_3$ | H | 34.8 | $Et_2O$-Hexane | 179–180 |
| 39 | tetrahydronaphthyl | phenyl-$CF_3$ | H | 48.8 | $CH_2Cl_2$-EtOH | 198–199 |

EXAMPLE 40

DMF (1 drop) was added to a solution of 1-naphthoic acid (900 mg) in THF (10 ml), followed by addition of oxayly chloride (0.49 ml) and stirring at room temperature for 2 hours. After replacing the solvent with acetone (10 ml), a solution of ammonium thiocyanate (436 mg) in acetone (5 ml) was added to the solution, followed by heating over a warm water bath for 1 minute and stirring at room temperature for 20 minutes. Then, a solution of 2-amino-4-(5,6,7,8-tetrahydro-2-naphthyl)-thiazole (1,00 g) in acetone (10 ml) was added to the mixed solution, which was then stirred at room temperature for 16 hours. The reaction solution was poured into water, and the crystals which separated out were recovered by filtration and washed with diethyl ether. Recrystallization from dichloroethane-ethanol produced 1-(1-naphthoyl)-3-[4-(5,6,7,8-tetrahydro-2-naphthyl)-2-thiazolyl]thiourea (yield of 875 mg, 45.4%) in the form of colorless needles. m.p. 216°–217° C.

EXAMPLES 41 TO 45

By following the same procedure as described in Example 40, there were obtained the compounds as shown in Table 4.

TABLE 4

$$\underset{R^1}{\overset{A}{\diagdown}}\underset{S}{\diagup}\underset{}{\overset{}{\diagdown}}\underset{}{\overset{N}{\diagup}}\text{NHCSNHCO}-B$$

| Example No. | A | B | $R^1$ | Yield % | Recryst'n. solvent | m.p. °C. |
|---|---|---|---|---|---|---|
| 41 | tetrahydronaphthyl | 2,4-di-Me-phenyl | H | 43.3 | $CH_2Cl_2$-EtOH | 189–190 |
| 42 | tetrahydronaphthyl | 2,5-di-Me-phenyl | H | 49.4 | $CH_2Cl_2$-EtOH | 193–194 |

TABLE 4-continued

Structure: A-C(R¹)=C(S-)-C(=N-)-NHCSNHCO-B (thiazole ring)

| Example No. | A | B | R¹ | Yield % | Recryst'n. solvent | m.p. °C. |
|---|---|---|---|---|---|---|
| 43 | tetrahydronaphthyl | 2,6-dimethylphenyl | H | 43.8 | CH₂Cl₂-EtOH | 192-193 |
| 44 | tetrahydronaphthyl | 4-ethylphenyl | H | 48.7 | CH₂Cl₂-EtOH | 196-197 |
| 45 | tetrahydronaphthyl | 4-isopropylphenyl | H | 47.9 | CH₂Cl₂-EtOH | 185-186 |

EXAMPLE 46

By following the same procedure as described in Example 1, there was naphthyl)-2-thiazolyl]thiourea. Yield, 81.4%. m.p. 235°-236° C. (dichloromethane-ethanol)

EXAMPLES 47 THROUGH 57

By following the same procedure as described in Example 23, there were obtained the compounds as shown in Table 5.

TABLE 5

Structure: A-C(R¹)=C(S-)-C(=N-)-NHCSNHCO-B (thiazole ring)

| Example No. | A | B | R¹ | Yield % | Recryst'n. solvent | m.p. °C. |
|---|---|---|---|---|---|---|
| 47 | tetrahydronaphthyl | 2-(trifluoromethyl)phenyl | H | 52.5 | CH₂Cl₂-EtOH | 230-231 |
| 48 | tetrahydronaphthyl | 2,4,6-trimethylphenyl | H | 50.9 | CH₂Cl₂-EtOH | 181-182 |
| 49 | tetrahydronaphthyl | biphenyl | H | 59.5 | CH₂Cl₂-EtOH | 223-224 |
| 50 | tetrahydronaphthyl | 4-(COOMe)phenyl | H | 34.8 | CH₂Cl₂-EtOH | 218-219 |
| 51 | tetrahydronaphthyl | 2-chlorophenyl | H | 54.4 | CH₂Cl₂-EtOH | 224-225 |

TABLE 5-continued
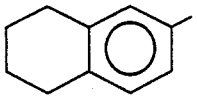
| Example No. | A | B | R¹ | Yield % | Recryst'n. solvent | m.p. °C. |
|---|---|---|---|---|---|---|
| 52 | 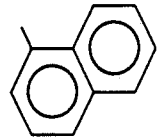 | 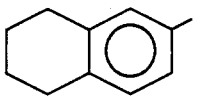 | Et | 47.3 | $CH_2Cl_2$-EtOH | 193–194 |
| 53 | 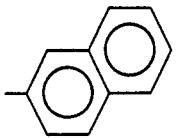 | 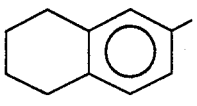 | Et | 59.1 | $CH_2Cl_2$-EtOH | 212–213 |
| 54 | 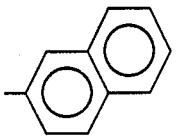 | 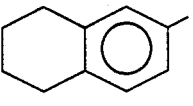 | Et | 60.7 | $CH_2Cl_2$-EtOH | 225–226 |
| 55 | 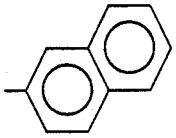 | 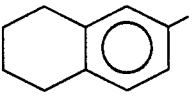 | Et | 57.9 | $CH_2Cl_2$-EtOH | 209–210 |
| 56 | 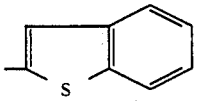 | 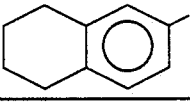 | H | 49.6 | $CH_2Cl_2$-EtOH | 210–211 |
| 57 | 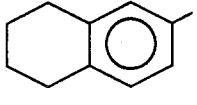 | Me | H | 16.1 | $CH_2Cl_2$-EtOH | 228–229 |
EXAMPLES 58 TO 71
By following the same procedure as described in Example 40, there were obtained the compounds as shown in Table 6.
TABLE 6
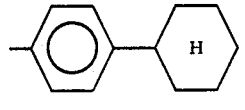
| Example No. | A | B | R¹ | Yield % | Recryst'n. solvent | m.p. °C. |
|---|---|---|---|---|---|---|
| 58 | 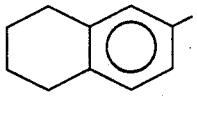 | 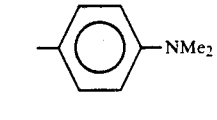 | H | 51.9 | $CH_2Cl_2$-EtOH | 207–208 |
| 59 |  | —$NMe_2$ | H | 16.4 | $CH_2Cl_2$-EtOH | 219–220 |

TABLE 6-continued $$\underset{R^1}{\overset{A}{\underset{S}{\bigvee}}}\overset{N}{\underset{\text{NHCSNHCO}-B}{\bigvee}}$$

| Example No. | A | B | $R^1$ | Yield % | Recryst'n. solvent | m.p. °C. |
|---|---|---|---|---|---|---|
| 60 | tetrahydronaphthyl | tetrahydronaphthyl | H | 58.4 | $CH_2Cl_2$-EtOH | 208–209 |
| 61 | tetrahydronaphthyl | phenyl-$OCF_3$ | H | 43.9 | $CH_2Cl_2$-EtOH | 183–184 |
| 62 | tetrahydronaphthyl | phenyl-CN | H | 32.2 | $CH_2Cl_2$-EtOH | 224–225 |
| 63 | tetrahydronaphthyl | anthracenyl | H | 51.7 | $CH_2Cl_2$-EtOH | 180–181 |
| 64 | tetrahydronaphthyl | phenanthrenyl | H | 37.8 | $CHCl_3$-EtOH | 220–221 |
| 65 | tetrahydronaphthyl | methylenedioxyphenyl | H | 30.6 | $CH_2Cl_2$-EtOH | 226–227 |
| 66 | tetrahydronaphthyl | Me,OMe,OMe-phenyl | H | 31.4 | $CH_2Cl_2$-EtOH | 224–225 |
| 67 | tetrahydronaphthyl | Me-naphthyl | H | 49.3 | $CH_2Cl_2$-EtOH | 227–228 |
| 68 | tetrahydronaphthyl | Me-naphthyl | H | 53.7 | $CH_2Cl_2$-EtOH | 223–224 |
| 69 | tetrahydronaphthyl | benzofuranyl | H | 49.9 | $CHCl_3$-DMF | 242–243 |

TABLE 6-continued

Structure:
A-C=C(R¹)-S-C(=N)-NHCSNHCO—B

| Example No. | A | B | R¹ | Yield % | Recryst'n. solvent | m.p. °C. |
|---|---|---|---|---|---|---|
| 70 | tetrahydronaphthyl | 4-Cl-phenyl with N=C-O-Me oxazoline | H | 32.1 | CH₂Cl₂-EtOH | 234–235 |
| 71 | tetrahydronaphthyl | 2-phenyl-thiazolyl | H | 40.3 | CH₂Cl₂-EtOH | 252–253 |

EXAMPLE 72

2-Ethylexanoyl chloride (0.43 g) was added to a solution of potassium thiocyanate (0.506 g) in dioxane (10 ml), followed by stirring at 55° to 60° C. for 4 hours. Then, 2-amino-4-(5,6,7,8-tetrahydro-2-naphthyl)-thiazole (0.5 g) was added to the solution, which was stirred at 55° to 60° C. for 3 hours. The reaction mixture was poured into water, and the crystals which separated out were recovered by filtration, washed with water and isopropyl ether, successively, and recrystallized from dichloromethane-isopropyl ether to give 1-(2-ethylhexanoyl) 3-[4-(5,6,7,8-tetrahydro-2-naphthyl)-2-thiazolyl]thiourea (0.438 g, 58.1%) in the form of colorless needles. m.p. 178°–179° C.

Elemental analysis, for C₂₂H₂₉N₃O₂S₂ Calcd: C, 63.58; H, 7.03; N, 10.11; Found: C, 63.45; H, 7.05; N, 10.14.

EXAMPLES 73 TO 75

By following the same procedure as described in Example 72, there were obtained the compounds as shown in Table 7.

TABLE 7

Structure:
A-C=C(R¹)-S-C(=N)-NHCSNHCO—B

| Example No. | A | B | R¹ | Yield % | Recryst'n. solvent | m.p. °C. |
|---|---|---|---|---|---|---|
| 73 | tetrahydronaphthyl | —CHMe₂ | H | 22.2 | CH₂Cl₂-EtOH | 208–209 |
| 74 | tetrahydronaphthyl | —CMe₃ | H | 24.0 | CH₂Cl₂-(iPr)₂O | 174–175 |
| 75 | tetrahydronaphthyl | —(CH₂)₅Me | H | 36.7 | CH₂Cl₂-(iPr)₂O | 183–184 |

We claim:

1. A thiourea compound of the formula:

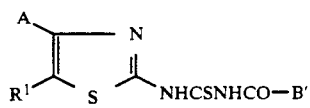

wherein A is a condensed aromatic ring group selected from (1) naphthyl which may be partly saturated, (2) anthryl which may be partly saturated, (3) $C_{6\text{-}14}$ aryl which may be partly saturated condensed with a 5 to 6 membered aromatic heterocyclic ring containing 1 to 4N, O and/or S atom(s) as the ring-forming hetero atom(s) which may be partly or wholly saturated and (4) 5 to 6-membered aromatic heterocyclic ring containing 1 to 4N, O and/or S atom(s) as the ring-forming hetero atom(s), which may be partly saturated, condensed with a $C_{16-14}$ aryl, which may be partly saturated; the condensed aromatic ring being unsubstituted or substituted by one to four substituent(s) selected from a group $S^1$ consisting of (1) $C_{1-10}$ alkyls which may be substituted by halogens; (2) hydroxyls which may be substituted by $C_{1-10}$ alkyls, phenyl-$C_{1-4}$ alkyls, and/or $C_{2-8}$ alkanoyls; (3) thiols which may be substituted by $C_{1-10}$ alkyls, phenyl-$C_{1-4}$ alkyls, and/or $C_{2-8}$ alkanoyls; (4) formyl; (5) $C_{2-11}$ alkanoyls which may be substituted by halogens, $C_{1-6}$ alkoxys and/or phenyls which may be substituted by halogens, $C_{1-6}$ alkyls and/or $C_{1-6}$ alkoxys; (6) amines which may be substituted by $C_{1-6}$ alkyls which may be substituted by $C_{1-6}$ alkylthios and/or halogens; (7) $C_{2-11}$ alkanoylaminos which may be substituted by halogens, $C_{1-6}$ alkoxys, $C_{1-6}$ alkylthios and/or hydroxyl; (8) aromatic ring groups selected from $C_{6-14}$ aryl groups and 5 to 6 membered aromatic heterocyclic ring groups containing 1 to 4N, O and/or S atom(s) as the ring forming hetero atom(s), each of which may be partially saturated and each of which may be unsubstituted or substituted by halogens, nitro, amino, $C_{1-6}$ alkanoylamino, $C_{1-6}$ alkoxys, $C_{1-6}$ alkylthios, and/or hydroxyl; (9) a condensed aromatic ring group selected from (a) naphthyl which may be partly saturated, (b) anthryl which may be partly saturated, (c) $C_{6-14}$ aryl which may be partly saturated, condensed with a 5 to 6 membered aromatic heterocyclic ring containing 1 to 4N, O and/or S atom(s) as the ring-forming hetero atom(s), which may be partly or wholly saturated, and (d) 5 to 6 membered aromatic heterocyclic ring which may be partly saturated, containing 1 to 4N, O and/or S atom(s) as the ring-forming hetero atom(s), condensed with a $C_{6-14}$ aryl which may be partly saturated; the condensed aromatic ring being unsubstituted or substituted by halogens, nitro, amino, $C_{1-6}$ alkanoylamino, $C_{1-6}$ alkoxys, $C_{1-6}$ alkylthios, and/or hydroxyl; (10) halogens; (11) cyano; (12) $C_{2-11}$ alkoxycarbonyl which may be substituted by halogens (13) $C_{6-14}$ aryloxycarbonyl which may be substituted by halogens and (14) nitro; $R^1$ is (1) a hydrogen atom; (2) $C_{1-10}$ alkyl which may be substituted by one to three substituent(s) selected from a group $S^2$ consisting of phenyl, halogens, $C_{1-6}$ alkoxys, $C_{1-6}$ alkylthios and/or $C_{2-8}$ alkanoylamino; or (3) a $C_{6-14}$ aryl which may be substituted by one to three substituent(s) selected from the group $S^1$ as defined above, or may combine with A to form a dihydronapthalene, dihydrophenanthrene, indene, 5,6-dihydro-1H-benzo-cycloheptane, or quinoline; B' is (1) a group represented by $OR^2$ wherein $R^2$ is a $C_{1-10}$ alkyl, a phenyl-$C_{1-4}$ alkyl, $C_{6-14}$ aryl, $C_{1-4}$ alkenyl, cinnamoyl, 3-(2-pyridyl)acryloyl, 3-(3-pyridyl)acryloyl, 3-(2-furyl)acryloyl, 4-phenyl-2-butenoyl or a $C_{1-4}$ alkynyl; (2) a $C_{1-10}$ alkyl, a $C_{1-4}$ alkenyl, a $C_{1-4}$ alkynyl, a phenyl-$C_{1-4}$ alkyl, cinnamoyl, 3-(2-pyridyl), 3-(3-pyridyl)acryloyl, 3-(2-furyl)acryloyl or 4-(phenyl-2-butenyl) or (3) the aromatic ring group as defined above for A; or a pharmaceutically acceptable salt thereof.

2. A compound according to claim 1, wherein A is naphthyl or a 5- to 6-membered aromatic heterocyclic containing 1 to 4N, O or S atoms as the ring-forming hetero atom condensed with a carbocyclic ring, each of which may be partially saturated and substituted by one to four substituent(s) selected from the group $S^1$.

3. A thiourea compound according to claim 1, wherein $R^1$ is a hydrogen atom.

4. A compound according to claim 1, wherein A is a 5,6,7,8-tetrahydro-naphthyl group.

5. A compound according to claim 1, wherein A is a 5,6,7,8-tetrahydronaphthyl group substituted by hydroxyl group.

6. A compound according to claim 1, which is 1-benzoyl-3-[4-(5,6,7,8-tetrahydro-2-naphthyl)-2-thiazolyl]-thiourea.

7. A compound according to claim 1, which is 1-benzoyl-3-[4-(5,6,7,8-tetrahydro-2-naphthyl)-5-ethyl-2-thiazolyl]thiourea.

8. A compound according to claim 1, which is 1-benzoyl-3-[4-(5,6,7,8-tetrahydro-2-naphthyl)-5-isopropyl-2-thiazolyl]thiourea.

9. A compound according to claim 1, which is 1-(4-fluorobenzoyl)-3-[4-(5,6,7,8-tetrahydro-2-naphthyl)-2-thiazolyl]thiourea.

10. A compound according to claim 1, which is 1-(2-methylbenzoyl)-3-[4-(5,6,7,8-tetrahydro-2-naphthyl)-2-thiazolyl]thiourea.

11. A compound according to claim 1, which is 1-(2-naphthoyl)-3-[4-(5,6,7,8-tetrahydro-2-naphthyl)-2-thiazolyl]thiourea.

12. A compound according to claim 1, which is 1-(2-thionaphthenyl)-3-[4-(5,6,7,8-tetrahydro-2-naphthyl)-2-thiazolyl]thiourea.

13. A compound according to claim 1, which is 1-(5,6,7,8-tetrahydro-2-naphthoyl)-3-[4-(5,6,7,8-tetrahydronaphthyl)-2-thiazolyl]thiourea.

14. A method for inhibiting AGE-formation which comprises administering to a patient in need thereof an effective-inhibitory amount of a thiourea compound of the formula:

$$\begin{array}{c} A \longrightarrow N \\ \parallel \quad \parallel \\ R^1 \diagdown S \diagup \diagdown NHCSNHCO-B' \end{array}$$

wherein A is an aromatic ring group selected from $C_{6-14}$ aryl groups which may be partly saturated, 5 to 6 membered heterocyclic ring groups containing 1 to 4N, O and/or S atom(s) as the ring forming hetero atom(s) which may be partly or wholly saturated, and condensed aromatic ring groups selected from (1) naphthyl which may be partly saturated, (2) anthryl which may be partly saturated, (3) $C_{6-14}$ aryl which may be partly saturated, condensed with a 5 to 6 membered aromatic heterocyclic ring which may be partly saturated containing 1 to 4N, O and/or S atom(s) as the ring-forming hetero atom(s) which may be partly or wholly saturated, wherein the condensed aromatic ring may be partly or wholly saturated and (4) 5 to 6 membered aromatic heterocyclic ring containing 1 to 4N, O and/or S atom(s) as the ring-forming hetero atom(s), which may be partly saturated, condensed with a $C_{6-14}$ aryl which may be partly saturated, wherein the aromatic ring group A is unsubstituted or substituted by one to four substituent(s) selected from a group $S^1$ consisting of (1) $C_{1-10}$ alkyls which may be substituted by halogens; (2) hydroxyls which may be substituted by $C_{1-10}$ alkyls, phenyl-$C_{1-4}$ alkyls, and/or $C_{2-8}$ alkanoyls; (3) thiols which may be substituted by $C_{1-10}$ alkyls, phenyl-$C_{1-4}$ alkyls, and/or $C_{2-8}$ alkanoyls; (4) formyl; (5) $C_{2-11}$ alkanoyls which may be substituted by halogens, $C_{1-6}$ alkoxys and/or phenyls which may be substituted by halogens, $C_{1-6}$ alkyls and/or $C_{1-6}$ alkoxys; (6) amines which may be substituted by $C_{1-6}$ alkyls which may be substituted by $C_{1-6}$ alkylthios and/or halogens; (7) $C_{2-11}$ alkanoylaminos which may be substituted by halogens, $C_{1-6}$ alkoxys, $C_{1-6}$ alkylthios and/or hydroxyl; (8) aromatic ring groups selected from $C_{6-14}$ aryl groups and 5 to 6 membered aromatic heterocyclic ring groups containing 1 to 4N, O and/or S atom(s) as the ring-forming hetero atom(s), each of which may be partially saturated and each of which may be unsubstituted or substituted by halogens, nitro, amino, $C_{1-6}$ alkanoylamino, $C_{1-6}$ alkoxys, $C_{1-6}$ alkylthios, and/or hydroxyl; (9) a condensed aromatic ring group selected from (a) naphthyl which may be partly saturated, (b) anthryl which may be partly saturated, (c) $C_{6-14}$ aryl which may be partly saturated condensed with a 5 to 6 membered aromatic heterocyclic ring which may be partly saturated containing 1 to 4N, O and/or S atom(s) as the ring-forming hetero atom(s) which may be partly or wholly saturated and (d) 5 to 6 membered aromatic heterocyclic ring which may be partly saturated containing 1 to 4N, O and/or S atom(s) as the ring-forming hetero atom(s), condensed with a $C_{6-14}$ aryl which may be partly saturated; the condensed aromatic ring being unsubstituted or substituted by halogens, nitro, amino, $C_{1-6}$ halogens; (11) cyano; (12) $C_{2-11}$ alkoxycarbonyl which may be substituted by halogens; (13) $C_{6-14}$ aryloxycarbonyl which may be substituted by halogens and (14) nitro; $R^1$ is (1) a hydrogen atom; (2) $C_{1-10}$ alkyl which may be substituted by one to three substituent(s) selected from a group $S^2$ consisting of phenyl, halogens, $C_{1-6}$ alkoxys, $C_{1-6}$ alkylthios and/or $C_{2-8}$ alkanoylamino; or (3) a $C_{6-14}$ aryl which may be substituted by one to three substituent(s) selected from the group $S^1$ as defined above, or may combine with A to form a dihydronapthalene, dihydrophenanthrene, indene, 5,6-dihydro-1H-benzo cycloheptane, or quinoline; B' is (1) a group represented by $OR^2$ wherein $R^2$ is a $C_{1-10}$ alkyl, a phenyl-$C_{1-4}$ alkyl, $C_{6-14}$ aryl, $C_{1-4}$ alkenyl, cinnamoyl, 3-(2-pyridyl)acryloyl, 3-(3-pyridyl)acryloyl, 3-(2-furyl)acryloyl, 4-phenyl-2-butenoyl or a $C_{1-4}$ alkynyl; (2) a $C_{1-10}$ alkyl, a $C_{1-4}$ alkenyl, a $C_{1-4}$ alkynyl, a phenyl-$C_{1-4}$ alkyl, cinnamoyl, 3-(2-pyridyl), 3(3-pyridyl)acryloyl, 3-(2-furyl)acryloyl or 4-(phenyl-2-butenyl) or (3) the aromatic ring group as defined above for A; or a pharmaceutically acceptable salt thereof.

* * * * *